(12) United States Patent
Sprinkle et al.

(10) Patent No.: US 7,722,572 B2
(45) Date of Patent: May 25, 2010

(54) SAFETY NEEDLE ASSEMBLY

(75) Inventors: Mark Sprinkle, Colora, MD (US);
Masahiko Kobayashi, Nakakoma (JP);
Christopher Bosel, Bloomington, IN (US)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 916 days.

(21) Appl. No.: 10/557,802

(22) PCT Filed: May 27, 2004

(86) PCT No.: PCT/US2004/016738

§ 371 (c)(1),
(2), (4) Date: Sep. 21, 2006

(87) PCT Pub. No.: WO2004/110517

PCT Pub. Date: Dec. 23, 2004

(65) Prior Publication Data

US 2007/0179451 A1   Aug. 2, 2007

Related U.S. Application Data

(60) Provisional application No. 60/473,474, filed on May 28, 2003.

(51) Int. Cl.
*A61M 5/32* (2006.01)
(52) U.S. Cl. ........................................ 604/192
(58) Field of Classification Search .......... 604/192–198, 604/263, 110, 162, 156, 117, 164.11
See application file for complete search history.

(56) References Cited

U.S. PATENT DOCUMENTS

| 5,584,816 A | 12/1996 | Gyure et al. |
| 5,913,846 A | 6/1999 | Szabo |
| 6,719,737 B2* | 4/2004 | Kobayashi .................. 604/263 |

OTHER PUBLICATIONS

International Search Report dated Sep. 7, 2005.
Written Opinion of the International Searching Authority dated Sep. 7, 2005.

* cited by examiner

*Primary Examiner*—Manuel A Mendez
(74) *Attorney, Agent, or Firm*—Buchanan Ingersoll & Rooney PC (57) ABSTRACT

A safety needle assembly includes a needle holder assembly, a cannula fixed to the needle holder assembly, a protector positioned over the cannula and removable to expose the cannula, and a sheath. The sheath is pivotally mounted on the needle holder assembly to permit the sheath to be pivoted relative to the needle holder assembly in a direction toward the cannula from a non-covering position in which the cannula is exposed after removal of the protector to a covering position in which the cannula is covered by the sheath. The sheath can also be provided with flat surfaces adapted to successively engage a portion of the needle holder assembly as the sheath is pivoted relative to the needle holder assembly. The needle holder assembly can include a tubular syringe barrel or a tubular needle holder adapted to receive an evacuated tube.

17 Claims, 3 Drawing Sheets

SAFETY NEEDLE ASSEMBLY

This application is based on and claims priority under 35 U.S.C. §119(e) with respect to U.S. provisional application No. 60/473,474 filed on May 28, 2003, the entire content of which is incorporated herein by reference. This application is also a U.S. national stage application of international application no. PCT/US2004/016738 filed on May 27, 2004, the entire content of which is incorporated herein by reference.

FIELD OF THE INVENTION

The present invention generally relates to needle assemblies or needle devices. More particularly, the present invention pertains to a safety mechanism for use in connection with needle assemblies or needle devices used to, for example, administer medication or withdraw a fluid, including hypodermic needles, catheter needles, blood collecting needles and other needle assemblies.

BACKGROUND DISCUSSION

Needle assemblies provided with a piercing element are used in a wide variety of contexts to administer medication and withdraw fluids. These needle assemblies include, by way of example, hypodermic needles, catheter needles and blood collecting needles. It is recognized in the medical community that it is preferable to utilize a needle assembly which is safe and readily easy to use.

In the past, to provide a measure of safety, needle assemblies have included a rigid cylindrical cap positioned over the cannula and engaging the device to which the cannula is connected. During use, the cylindrical cap is removed to expose the cannula. After using the needle assembly for its intended purpose, the cylindrical cap must be once again mounted on the hub to cover the used cannula. Oftentimes, the healthcare professional tries to reposition the cylindrical cap on the needle assembly by "scooping" the cylindrical cap with the needle assembly. As can be appreciated, this may not be an easy or effective technique for repositioning the protective cap on the needle assembly. Also, the cap may become accidentally dislodged from the needle assembly, thus exposing the used cannula and presenting a potential danger.

Other proposals have also been made to incorporate safety attributes into needle assemblies. These proposals are generally divided into three categories: 1) hinged recap devices in which a hinged sleeve is pivoted into a permanently locked position with respect to the cannula; 2) retractable cannula devices in which the cannula is retracted into the syringe barrel or the syringe plunger; and 3) sliding barrel devices in which the syringe barrel is formed by two concentric cylinders, the outer one of which is slid by the health care worker towards the cannula after use to cover the cannula. Although these assemblies provide some additional measure of safety, difficulties remain.

For example, hinged recap devices may be assembled between the syringe and needle assembly. This construction introduces dead space between the cannula and the syringe, thereby resulting in the waste of expensive medication. Retractable cannula devices run the risk of inadvertently retracting, thus wasting a syringe and once again presenting the possibility of wasting expensive medication. Additionally, the velocity of the cannula retraction could result in the spraying or splashing of fluids or medication, thus actually increasing the healthcare professional's exposure risk. The sliding barrel design is disadvantageous in that it almost doubles the length of the syringe from the unused position to the used/disabled/engaged position, thus substantially increasing the volume of biohazard waste and possibly creating exposure hazards because the syringe/needle assembly does not adequately fit into the sharps container.

In light of at least the foregoing, a need exists for a safety needle assembly that is constructed to provide desirable safety characteristics while also being constructed to facilitate usage by the user.

SUMMARY

A safety needle assembly comprises a tubular needle holder possessing a proximal end portion and a distal end portion, a cannula fixed to the distal end portion of the tubular needle holder and provided with a lumen, and a collar formed separately from the tubular needle holder and rotatably mounted on the tubular needle holder to rotate relative to the tubular needle holder, with the collar being provided with a pair of spaced apart mounting ears each provided with a hole. A protector is positioned over the cannula and covers the distal end of the cannula. The protector has an open end and an oppositely located closed end, and is removable to expose the cannula including the distal end. A sheath is provided with an opening extending along at least a portion of a longitudinal extent of the sheath providing access to the interior of the sheath. The sheath comprises a pin mount and a pair of pins extending from the pin mount, with each of the pins being positioned in a respective one of the holes in the ears of the collar so that the sheath is pivotally mounted on the collar. The sheath is positioned outside the protector when the protector is positioned over the cannula and is pivotable towards the cannula after removal of the protector so that the cannula moves into the interior of the sheath and is covered by the sheath. The pin mounting portion of the sheath comprises a plurality of flat surfaces which engage a portion of the collar located between the mounting ears during pivoting movement of the sheath.

According to another aspect, a safety needle assembly comprises a tubular needle holder, a cannula fixed to the tubular needle holder and provided with a lumen, and a protector positioned over the cannula and covering the distal end of the cannula, with the protector having an open end to permit the protector to be placed in covering relation to the cannula and being removable to expose the cannula. A sheath possesses an opening extending along at least a portion of a longitudinal extent of the sheath which provides access to an interior of the sheath, with the sheath being pivotally mounted with respect to the needle holder to permit the sheath, upon application of a force, to be pivoted in a direction toward the cannula from a non-covering position in which the cannula is exposed after removal of the protector to a covering position in which the cannula is covered by the sheath. The sheath possesses at least one locking tab adapted to engage the cannula when the sheath is sufficiently pivoted toward the cannula to permanently lock the sheath in a locked position relative to the cannula to prevent the sheath from pivoting back towards the non-covering position. The sheath comprises means for causing the sheath to automatically pivot in a direction away from the cannula when the force is removed prior to the cannula being engaged by the locking tab to thereby indicate that the locking tab has not engaged the cannula and the sheath is not in the locked position.

According to a further aspect, a safety needle assembly comprises a needle holder assembly, a cannula fixed to the needle holder assembly and provided with a lumen, and a protector positioned over the cannula and covering the distal end of the cannula. The protector has an open end to permit the protector to be placed in covering relation to the cannula, and the protector is removable to expose the cannula. A sheath possesses an opening extending along at least a portion of a longitudinal extent of the sheath which provides access to the interior of the sheath. The sheath is pivotally mounted on the needle holder assembly to permit the sheath to be pivoted relative to the needle holder assembly in a direction toward the cannula from a non-covering position in which the cannula is exposed after removal of the protector to a covering position in which the cannula is covered by the sheath. The sheath comprises a plurality of flat surfaces adapted to successively engage a portion of the needle holder assembly as the sheath is pivoted relative to the needle holder assembly.

BRIEF DESCRIPTION OF THE DRAWING FIGURES

The foregoing and additional features and characteristics of the present invention will become more apparent from the following detailed description considered with reference to the accompanying drawing figures in which like reference numerals designate like elements.

DETAILED DESCRIPTION

Figures 1, 2, 3, 4, 5, 6:
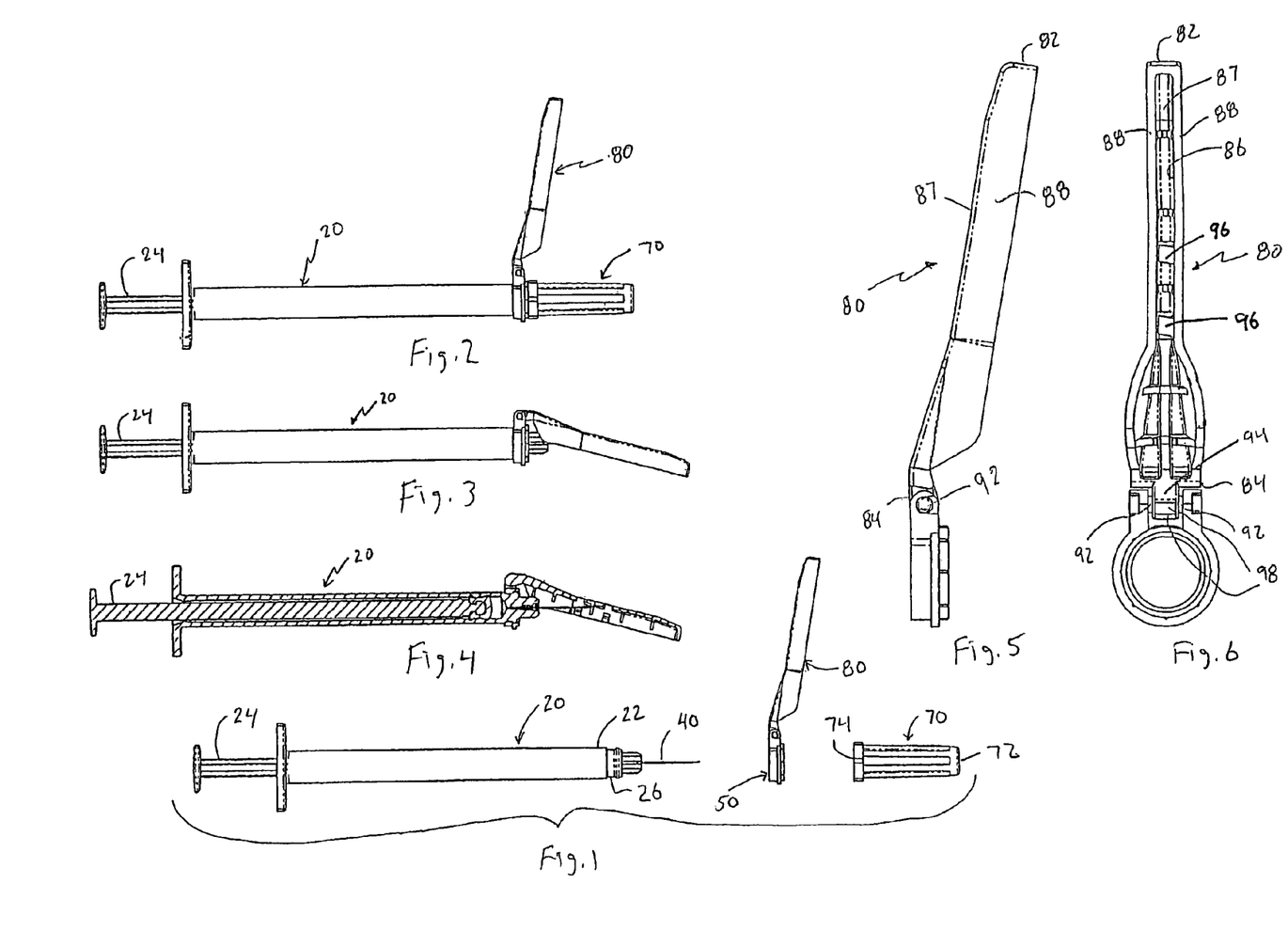
FIG. 1 is an exploded side view of the components forming the safety needle assembly of the present invention.
FIG. 2 is a side view of the safety needle assembly shown in FIG. 1 illustrating the components in an assembled condition.
FIG. 3 is a side view similar to FIG. 2 illustrating the safety needle assembly with the protector removed.
FIG. 4 is a cross-sectional view of the safety needle assembly shown in FIG. 3 with the sheath in a covering position.
FIG. 5 is a side view of the sheath, connected to the collar, forming a part of the safety needle assembly.
FIG. 6 is a front view of the sheath and collar shown in FIG. 5.

The safety needle assembly according to the present invention is useful in the context of a fluid transfer device such as a syringe for delivering fluid (e.g., medication) or another type of needle holder such as one adapted to receive an evacuated tube for purposes of drawing a blood sample. Referring initially to FIG. 1 which illustrates the safety needle assembly used in the context of a fluid transfer device in the form of a syringe, the safety needle assembly includes a syringe 20, a cannula 40, a collar 50, a protector 70 and a sheath 80. The syringe 20 includes a tube or syringe barrel 22, constituting a tubular needle holder, and a plunger 24. The proximal end of the cannula 40 is connected to the distal end of the syringe barrel 22 in a typical manner such as through the use of an adhesive such as a light curing acrylic or a heat curing epoxy. The cannula 40 is provided with a lumen that communicates with the interior of the syringe barrel 22. The distal end of the cannula 40 forms a patient end of the cannula and is beveled in a known manner.

The syringe barrel 22, the collar 50, the protector 70 and the sheath 80 are preferably each formed through molding and as respective one-piece parts. Thus, the syringe barrel 22, including the distal end to which the proximal end of the cannula 40 is connected, is formed as an integral, one-piece syringe barrel in which all of the features forming the syringe barrel 22 are formed at the same time. Similarly, the collar 50 including all of the features described below is formed as an integral, one-piece collar in which all of the features forming the collar 50 are formed at the same time, the protector 70 including all of the features described below is formed as an integral, one-piece protector in which all of the features forming the protector are formed at the same time, and the sheath 80 including all of the features described below is formed as an integral, one-piece sheath in which all of the features forming the sheath as described below are formed at the same time.

The collar 50 is adapted to be mounted on the outer surface of the syringe barrel 22 by moving the collar 50 over the cannula 40 and into place on the outer surface of the distal end portion of the syringe barrel 22 in the manner described in more detail below. In addition, the protector 70 is adapted to be moved over the cannula 40 and positioned in covering relation to the cannula 40 so that the cannula 40 in enclosed within the protector 70. Further, as described in more detail below, the sheath 80 is adapted to be mounted on the collar 50 in a manner that allows the sheath 80 to be pivoted relative to the collar 50 and the syringe.

As illustrated in FIG. 1, the distal end portion of the syringe barrel 22 is provided with a collar mounting region 26. In the illustrated embodiment, the collar mounting region 26 is in the form of an annular groove or recess provided at the outer surface of the syringe barrel 22. The groove or recess 26 is positioned proximally of the distal-most end of the syringe barrel from which the cannula 40 extends. The groove 26 is adapted to receive the collar 50 so that once the collar 50 is mounted in the groove 26, the collar 50 cannot be inadvertently removed from the syringe barrel 22. To help achieve this result, axially spaced apart ridges are provided on the syringe barrel 22 and are located on opposite axial ends of the groove 26. Also, as shown in FIG. 1, the portion of the outer surface of the syringe barrel 22 located immediately distal of the groove 26 is inclined or sloped to facilitate axial placement of the collar 50 in the groove 26. That is, the portions of the syringe barrel 22 immediately adjoining the axial ends of the annular groove 26 each possess an outer diameter greater than the outer diameter of the annular groove 26.

Referring to FIGS. 7-10, the collar 50 is annularly shaped, having a proximal end 52 and a distal end 54. The annular collar 50 is also provided with a centrally located through-hole for allowing the collar 50 to be mounted on the syringe barrel 22. The internal surface of the collar 50 is adapted to face the outer surface of the groove 26 on the syringe barrel 22 when the collar 50 is mounted on the groove 26. The collar 50 is able to rotate relative to the syringe barrel 22. Of course, it is to be understood that the collar could also be fixed against rotation, for example through the use of a suitable adhesive, by providing the inner surface of the collar 50 and the outer surface of the barrel 22 with teeth/recesses that engage one another, or using other appropriate means.

Figure 8:
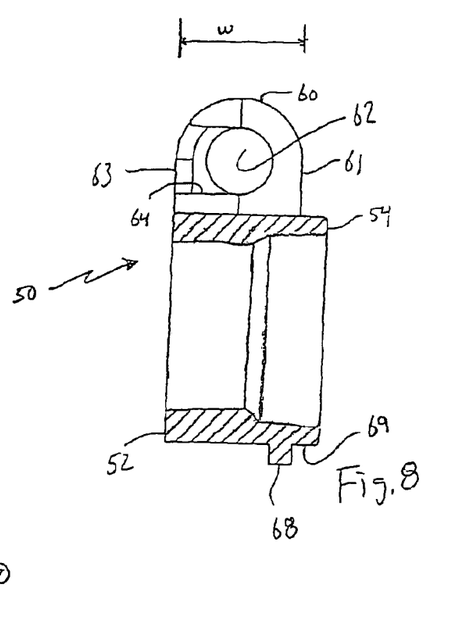
FIG. 8 is a cross-sectional view of the collar shown in FIG. 7.

As generally seen in FIG. 8, the inner surface of the annular collar 50 has a somewhat smaller inner diameter over the portion of the collar closer to the proximal end 52 and has a somewhat larger inner diameter over the portion of the collar closer to the distal end 54. The smaller inner diameter portion is adapted to be seated in the groove 26 in the syringe barrel 22. The smaller inner diameter portion of the collar possesses an internal diameter that is less than the outer diameter of the axially spaced apart ridges provided at the opposite ends of the groove 26 on the syringe barrel 22. This arrangement for seating of the collar 50 in the groove 26 could also be achieved by providing an annular arrangement of radially inwardly directed projections that engage the groove 26.

Figure 7:
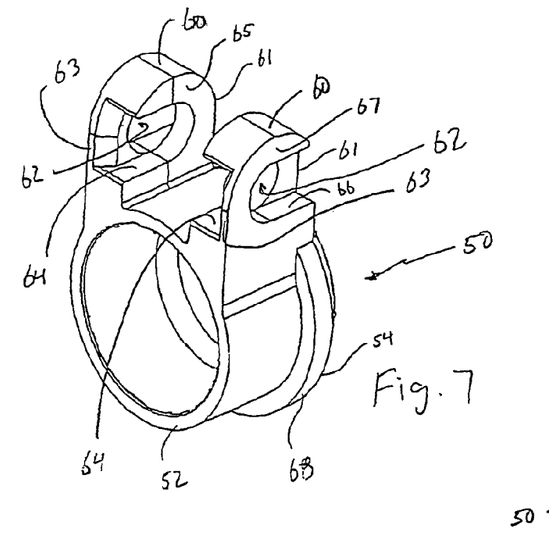
FIG. 7 is an enlarged rear perspective view of the collar used in the safety needle assembly shown in FIG. 1.

The annular collar 50 is also provided with a pair of spaced apart and outwardly directed sheath mounting ears 60. These sheath mounting ears 60 provide a part of the mechanism for pivotally or hingedly connecting the sheath 80 to the collar 50 so that the sheath 80 can pivot relative to the collar 50, as well as the cannula and syringe barrel.

Figure 9:
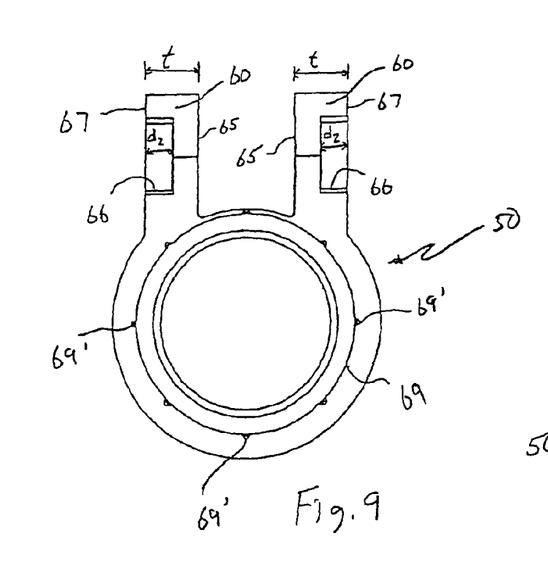
FIG. 9 is a front end view of the collar shown in FIG. 7.

Each of the mounting ears 60 includes a distal end 61 and proximal end 63. Further, each of the mounting ears 60 is provided with a first side surface 65 forming an inner side surface and a second side surface 67 forming an outer side surface. The first side surfaces or inner side surfaces 65, 65 of the two mounting ears 60 face towards one another. Thus, as seen in FIG. 9, each of the mounting ears 60 possesses a thickness t represented by the distance between the first and second side surfaces 65, 67. In addition, as shown in FIG. 8, each of the mounting ears 60 possesses a width w represented by the distance between the proximal end 63 and the distal end 61 of the mounting ears 60.

Each of the mounting ears 60 is provided with a through hole 62. The through-hole 62 in each of the mounting ears 60 is formed by virtue of a first groove 64 provided at the inner side surface 65 of each mounting ear 60 and a second groove 66 provided at the outer side surface 67 of each mounting ear 60.

Described in more detail, the first groove 64 formed at the inner side surface 65 of each mounting ear 60 extends from the proximal end 63 of the mounting ear 60 towards the distal end 61 of the mounting ear. The first grooves 64 open to the proximal end 63 of the mounting ears 60, but stop short of the distal end 61 of the mounting ears 60. The second groove 66 formed at the outer side surface 67 of each mounting ear 60 extends from the distal end 61 of the mounting ear towards the proximal end 63 of the mounting ear 60. The second grooves 66 open to the distal end of the mounting ear 60, but stop short of the proximal end 63 of the mounting ear 60. As can be seen from FIG. 7, the first and second grooves 64, 66 on each of the mounting ears 60 overlap one another with respect to the width-wise extent of the mounting ears 60.

Figure 10:
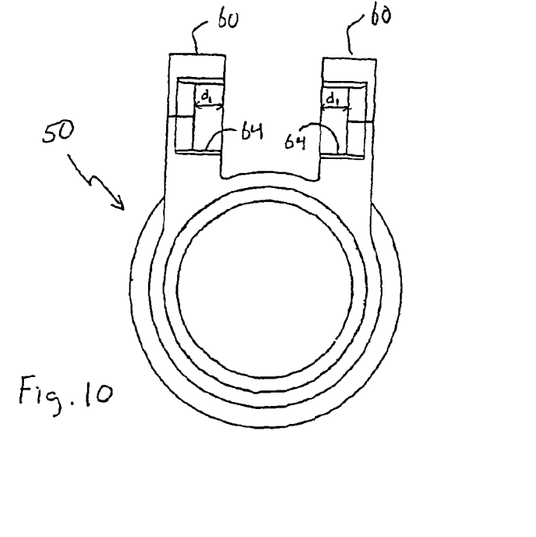
FIG. 10 is a rear end view of the collar shown in FIG. 7.

The length of the first and second groove 64, 66 (i.e., the dimension of the grooves 64, 66 in the width-wise direction of the mounting ears 60) in conjunction with the depth d1, d2 of the first and second grooves 64, 66 (i.e., the dimension of the grooves 64, 66 in the thickness direction of the mounting ears 60 depicted in FIGS. 9 and 10) are specifically selected so that in the region of overlap of the first and second grooves 64, 66, the respective through-holes 62 are formed.

The combined depth (d1+d2) of the first and second grooves 64, 66 on each of the mounting ears 60 is at least equal to the thickness t of the respective mounting ears 60, and is preferably slightly greater than the thickness t of the respective mounting ears 60. In this way, with the overlap of the first and second grooves 64, 66 in the width-wise direction of the mounting ears 60 as shown in FIG. 4, the through-holes 62 are automatically formed.

In the illustrated and described embodiment, the depths d1, d2 of the first and second grooves 64 in one mounting ear 60 are equal to one another, with each of the depths d1, d2 being at least equal to, and preferably slightly greater, than one-half the thickness t of the mounting ear 60. Similarly, the depths d1, d2 of the first and second grooves 64, 66 in the other mounting ear 60 are also equal to one another, with each of the depths d1, d2 being at least equal to, and preferably slightly greater, than one-half the thickness t of the mounting ear 60. Of course, the first and second grooves 64, 66 in each mounting ear 60 need not be equal to one another.

The combined length of the first and second grooves 64, 66 in the width-wise direction in each mounting ear 60 is greater than the width w of the respective mounting ear 60. In the illustrated and described embodiment, the length of each of the first and second grooves 64, 66 in each mounting ear 60 is greater than one-half the width w of the respective mounting ear 60 so that the first and second groove 64, 66 overlap one another as described above. By virtue of the configuration and arrangement of the grooves 64, 66 as described above, the through-hole 62 in each mounting ear 60 can be formed in a mold that is appropriately configured to form the grooves 64, 66 in each of the mounting ears 60. A more complicated mold configuration for forming the through-holes 62 is thus not required.

As seen in FIGS. 7 and 8, the collar 50 is also provided with a radially outwardly directed annular ridge 68. This annular ridge 68 is located adjacent the distal end portion of the collar 50, but is spaced towards the proximal end 52 of the collar from the distal end 54. This thus defines a seating surface 69 which, as described in more detail below, is used to seat or mount the protector 70. A plurality of spaced apart protuberances 69' are disposed along the circumferential extent of the seating surface 69 to help facilitate mounting or seating of the protector 70 on the seating region 69. In addition, the annular ridge 68 forms a stop which engages the proximal end of the protector 70 when the protector is mounted on the seating region 69 of the collar 50.

Of, it is also to be understood that the protector could be mounted on and engage the distal end of the barrel rather than being mounted on the collar. In such a case, the seating surface 69 and the ridge 68 on the collar need not be provided.

As shown in FIG. 1, the protector 70 is formed as an elongated cylindrical hollow member having a distal end 72 and a proximal end 74. The protector 70 is open at the proximal end 74 and preferably closed at the distal end 72. An intermediate portion of the exterior surface of the protector 70 can be provided with longitudinal ribs to facilitate gripping by the user. The interior of the protector 70 at the proximal end 74 is provided with a seating surface so that when the protector 70 is positioned over the cannula 40 upon assembling the safety needle assembly, the seating surface of the protector 70 encircles the seating region 69 on the collar 50 and engages the protuberances 69'. In addition, the proximal end 74 of the protector contacts the annular ridge 68.

Referring to FIGS. 5 and 6, the sheath 80 is formed as a generally elongated member having a distal end 82 and a proximal end 84. The sheath 80 is provided with an opening 86 that extends along at least a portion of the longitudinal extent of the sheath 80 and communicates with the interior of the sheath 80. During use or operation of the safety needle assembly, as the sheath 80 is pivoted towards the cannula 40 (shown in FIG. 1), the cannula is adapted to pass through the opening 86 in the sheath and into the interior of the sheath 80. In the illustrated and described embodiment, the opening 86 in the sheath 80 extends along the entire longitudinal extent of the sheath 80 so that the sheath is completely open along one side.

The sheath 80 possesses a back wall 87 and two oppositely positioned side walls 88. The opening 86 in the sheath 80 is defined at the side of the sheath 80 opposite the back wall 87.

As further illustrated in FIG. 6, the proximal portion of each of the side walls 88 of the sheath 80 flares outwardly or is angled outwardly relative to the distal portion of the side wall. This arrangement makes it possible to position the sheath 80 closer to the protector 70, when the protector 70 is in covering relation to the cannula, than would otherwise be the case if the sidewalls 88 were not flared or angled outwardly.

The sheath 80 includes a collar connecting or mounting mechanism located at the proximal end 84 of the sheath 80. This collar mounting mechanism includes a pair of pins 92 extending in opposite directions from a pin mount 94. As described in more detail below, each of the pins 92 is adapted to be positioned in the through-hole 62 in one of the mounting ears 60 to pivotally mount or connect the sheath 80 on the collar 50. The pins can be provided with beveled end edges that help facilitate mounting the pins 92 in the through-holes 62 of the mounting ears 60.

The outer surface of the pin mount 94 can be provided with a plurality of flat surfaces 98 that are adapted to engage the portion of the outer surface of the collar 50 located between the mounting ears 60 during pivoting movement of the sheath 80. This produces a desirable clicking feeling when the sheath 80 is pivoted towards the cannula 40. The adjoining flat surfaces 98 on the pin mount 94 are angled relative to one another (i.e., form an angle other than zero degrees).

The interior of the sheath 80 is provided with one or more locking tabs 96 formed by punching through portions of the back wall 86 of the sheath 80 as shown in FIG. 6. These locking tabs 96 are able to flex when engaged by the cannula as sheath 80 is being pivoted towards the cannula 40 (shown in FIG. 1). The cannula is thus able to move past the tabs 96. Once the cannula has moved past the tabs 96, the cannula is prevented from moving back out of the interior of the sheath 80. The cannula is thus permanently locked within the interior of the sheath 80. This locking occurs automatically in that the movement of the cannula into the interior of the sheath 80 and past the locking tabs 96 is all that is necessary to permanently lock the cannula within the interior of the sheath 80.

In its assembled state, the safety needle assembly includes the cannula 40 shown in FIG. 1 connected to or mounted at the distal end 22 of the syringe barrel 22 so that the cannula is fixed relative to the syringe In addition, the collar 50 is mounted on the syringe barrel 22 so that the smaller inner diameter portion of the inner surface of the collar 50 is positioned in the groove 26 of the syringe barrel. The collar 50 is thus able to rotate relative to the syringe 20, although it could alternatively be fixed against rotation as noted above. Also, the protector 70 is removably positioned in covering relation to the cannula 40 so that the proximal end 74 of the protector 70 encircles the seating region 69 on the distal end of the collar 50, with the interior seating surface on the protector 70 engaging the protuberances 69' at the seating region 69. Further, the sheath 80 is connected to the collar 50 by virtue of the pins 92 on the sheath 80 being positioned in the through holes 62 in the mounting ears 60 of the collar 50. The assembled state of the safety needle assembly is shown in FIG. 2. The safety needle assembly shown in FIG. 2 can be packaged for shipment. In the packaged state, the sheath 80 would be pivoted forward into contacting relationship with the outer surface of the protector 70 so that the sheath 80 is located as close as possible to the central axis of the cannula.

To use the safety needle assembly, the user can initially pivot the sheath 80 away from the protector 70 to allow the protector 70 to be removed. During pivoting movement of the sheath 80, the aforementioned flat surfaces 98 on the pin mount 94 of the sheath 80 engage the outer surface of the collar 50 located between the mounting ears 60. This produces a clicking feeling to the user. In addition, the engagement of the flat surfaces 98 with the portion of the collar helps maintain the sheath 80 in the desired position. That is, the engagement of the flat surfaces 98 with the outer surface of the collar 50 inhibits the sheath 80 from pivoting on its own and so the sheath is not likely to interfere with the use of the cannula.

After pivoting the sheath 80 out of the way, the protector 70 is removed to expose the cannula 40 shown in FIG. 1. Once the protector 70 is removed, the user can use the cannula in the desired manner. During use, the collar 50 and the connected sheath 80 can be rotated relative to the syringe 20 to thus orient the sheath 80 in a desired position. This may be advantageous from the standpoint of allowing the user to position the sheath 80 at a rotational position relative to the syringe 20 that does not interfere with the use of the syringe. Some users, for example, may wish to have the bevel on the distal end of the cannula oriented in a particular direction, without having the position of the sheath 80 interfere with such usage. As noted previously though, the collar and the connected sheath 80 can be fixed against rotation relative to the syringe 20.

After the user has finished using the cannula, the sheath 80 is pivoted towards the cannula 40 (i.e., towards the closed or covering position) to safely cover the cannula. As the sheath 80 is pivoted towards the cannula, the engagement of the flat surfaces 98 on the pin mount 94 with the outer surface of the collar 50 located between the mounting ears 60, 60 once again results in a clicking feeling to the user so the user feels as though they have more control over the pivoting movement of the sheath 80. The sheath 80 continues to be pivoted towards the cannula 40 by the user until the cannula pushes past the locking tabs 96 and is permanently and automatically locked in place within the interior of the sheath 80 by the locking tabs. At this point, the cannula 40 is completely covered by the sheath. Further, the cannula cannot move back past the locking tabs 96 and so the cannula (including the beveled distal end) is considered to be safe. It is possible to configure and dimension the flat surfaces 98 on the pin mount of the sheath 80 so that as the sheath 80 is pivoted towards the closed position, if the pushing force applied to the sheath is removed (e.g., the user stops pivoting the sheath) at a point in which the sheath 80 is not pivoted sufficiently to cause the cannula to be locked behind the locking tabs 96, the flat surfaces 98 will cause the sheath to pivot backward slightly away from the cannula, thus providing an immediate indication that the sheath 80 has not been sufficiently pivoted towards the closed position to cause the cannula to be engaged behind the locking tabs 96.

The description provided above generally describes how the safety needle assembly is assembled. A more detailed description of this assembly procedure is set forth below. As an initial step, the proximal end of the cannula 40 is fitted into a hole provided at the distal end of the syringe barrel 22. The cannula 40 is then fixed in place relative to the syringe 20 in a typical manner such as through use of an adhesive such as a light curing acrylic or a heat curing epoxy.

According to one possibility, the next step involves mounting the collar 50 on the syringe barrel 22. This can be accomplished by, for example, vertically orienting the syringe barrel 22 and dropping the collar 50 onto the syringe barrel 22 from the distal end of the syringe barrel 22. Of course, it is not necessary to vertically orient the syringe barrel 22 to mount the collar 50 on the syringe barrel 22.

Another step in the assembly process is to position the protector 70 in covering relation to the cannula. This can be accomplished by simply placing the protector 70 over the cannula to cover the sharp bevel at the distal end of the cannula 40. In the illustrated and described embodiment of the safety needle assembly, the proximal end 74 of the protector 70 is mounted on the collar 50. More particularly, as described above, a seating surface at the proximal end 74 of the protector 70 surrounds the seating region 69 at the distal end of the collar 50 and engages the protuberances 69' located at the seating region 69. Also, the protector 70 is mounted on the collar 50 so that the proximal end 74 of the protector 70 contacts or engages the annular ridge or stop 68 on the collar 50. As noted above, it is also possible to mount the protector 70 on the distal end of the syringe barrel.

A further step in the assembly process involves mounting the sheath 80 on the collar 50 by connecting the collar connecting mechanism of the sheath 80 to the mounting ears 60 of the collar 50. This can be accomplished in a variety of ways. In one form, the sheath 80 can be moved in one motion along an arcuate path of movement to position the pins 92 of the sheath 80 in the through holes 62 of the mounting ears 60. As an alternative, the sheath 80 can be mounted on the collar 50 through use of two movements, one involving moving the sheath 80 towards the collar 50 in a direction perpendicular to the axis of the collar 50, and the other involving moving the sheath 80 towards the mounting ears 60 in a direction parallel to the axis of the collar.

Using either alternative or another motion, the sheath 80 is moved to align the pins 92 on the sheath 80 with the first grooves 64 on the inner side surfaces of the mounting ears 60. As the pins 92 move into the first grooves 64, the mounting ears 60 are spread apart slightly because the distance between the bottom surfaces of the first grooves 64 is less than the distance between the outer ends of the pins 92. The aforementioned beveled edges on the ends of the pins 92 help facilitate the introduction of the pins 92 into the first grooves 64. As the pins 92 move into the first grooves 64 and spread apart the mounting ears 60, the pins 92 pop into the through holes 62 in the mounting ears 60 so that the sheath is pivotally mounted on the collar 50.

Once all of the parts are assembled, the sheath 80 is pivoted towards the protector 70 until the sheath 80 contacts the outer surface of the protector 70. With the sheath 80 positioned in contacting engagement with the outer surface of the protector 70, the aforementioned outwardly angled or flared portions of the side walls 88 of the sheath 80 partially embrace and overlap the protector 70. This allows the sheath 80 to be positioned closer to the central axis of the cannula than would otherwise be the case if the outwardly angled or flared portions of the side walls 88 were not provided (i.e., if the side walls 88 of the sheath 80 were straight along their entire length). This can reduce packaging costs in that as the angle between the axis of the sheath and the axis of the cannula increases, the completed assembly occupies more space. Thus by reducing this angle, the assembly can be packaged more compactly.

It is possible to vary the assembly steps described above. For example, existing equipment in facilities that manufacture needles may already have in place equipment which mounts a rigid sleeve on the syringe to cover the cannula. To continue utilizing this equipment and avoid the need for completely redesigning the assembly equipment, the assembly steps can be varied from those described above.

Another embodiment of the safety needle assembly is shown in FIGS. 11-16. This embodiment differs from the embodiment described above in that instead of the fluid transfer device being the in the form of a syringe, the fluid transfer device is in the form of a tube that is adapted to receive an evacuated tube for use in, for example, drawing blood from a patient. Most other features of the safety needle assembly shown in FIGS. 11-16 are similar to those described above. Features generally corresponding to those described above are designated by the same reference numeral, except preceded with a "1".

As most of the features associated with the safety needle assembly shown in FIGS. 11-16 have already been described above, a detailed description of such features will not be repeated. The following discussion generally describes features associated with the embodiment of the safety needle assembly shown in FIGS. 11-16, including differences associated with this embodiment relative to the earlier described embodiment.

Figures 11, 12, 13, 14, 15, 16:
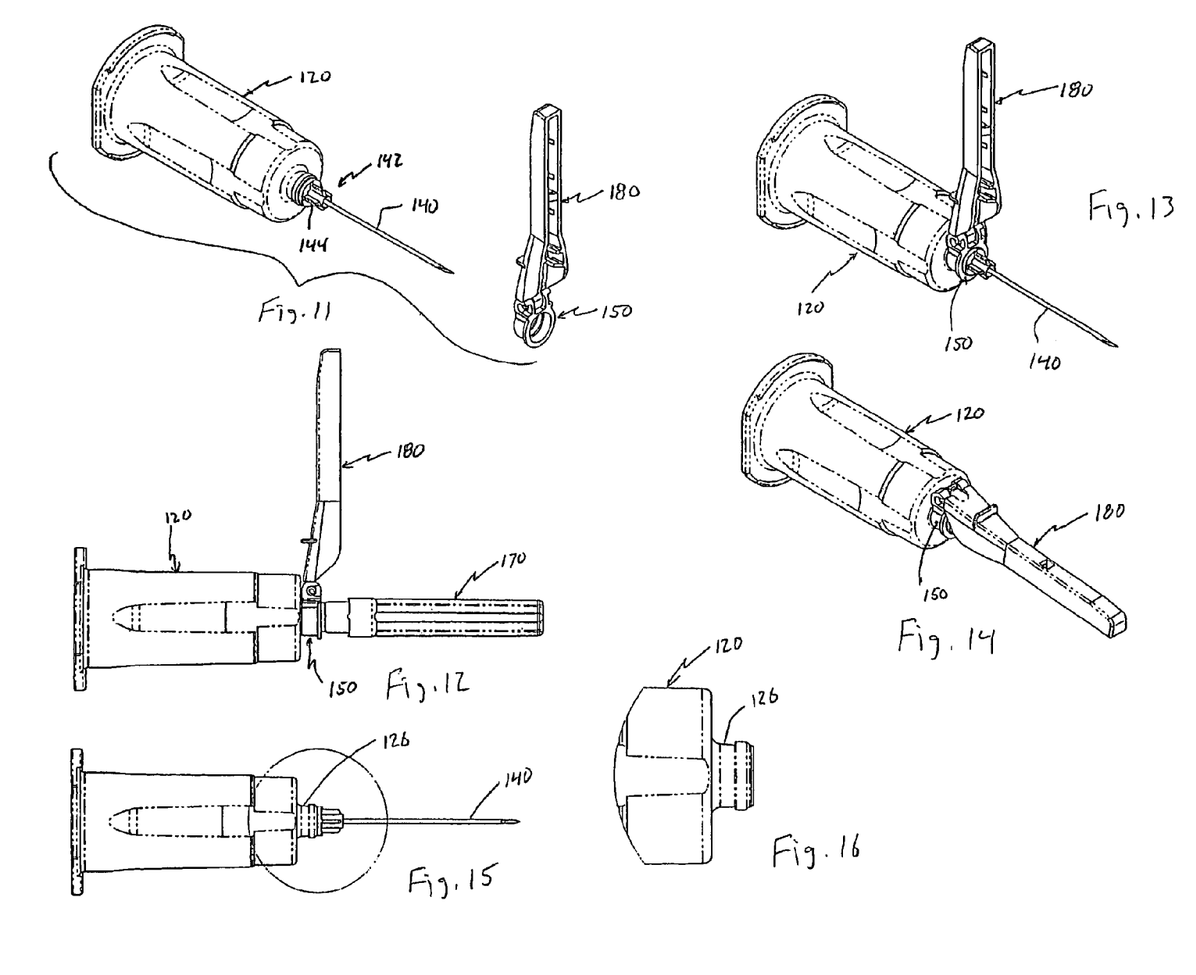
FIG. 11 is an exploded perspective view of components forming a part of the blood collection device according to another embodiment of the invention.
FIG. 12 is a side view of the blood collection device shown in FIG. 11 illustrating the components in an assembled condition, including the protector which is not shown in FIG. 11.
FIG. 13 is a perspective view of the blood collection device shown in FIG. 12 illustrating the blood collection device with the protector removed.
FIG. 14 is a perspective view of the blood collection device shown in FIG. 13 with the sheath pivoted to the cannula enclosing or covering position.
FIG. 15 is a side view of a portion of the blood collection device shown in FIG. 13.
FIG. 16 is an enlarged view of a portion of the circled region of the blood collection device illustrated in FIG. 15.

The illustrated embodiment of the safety needle assembly includes a tube or tubular needle holder 120, a cannula assembly 142 comprised of a cannula 140 and a hub 144, a collar 150, a protector 170 and a sheath 180. The tubular needle holder 120 has a hollow interior and is open at one end for receiving the evacuated tube. The cannula assembly 142 is secured to or mounted at the distal end of the tubular needle holder 120. The distal end of the cannula 140 projects away from the needle holder 120 and the proximal end of the cannula 140 extends into the interior of the needle holder 120 to communicate with the evacuated tube. In a known manner, the cannula assembly 142 includes a mechanism such as a valve that allows the distal end of the cannula 140 to remain in the patient with having blood discharge out the proximal end of the cannula 140. The proximal end of the cannula 140 located in the interior of the needle holder 120 can be covered, for example by a sleeve or the like.

The distal end portion of the needle holder 120 is provided with a collar mounting region 126. In the illustrated embodiment, the collar mounting region is in the form of a recessed region or groove 126 which is adapted to receive the collar 150. The groove 126 is configured in a manner similar to that described above. As illustrated in FIGS. 15 and 16, the groove 126 is located at a distal end portion of the needle holder 120 whose outer diameter is reduced relative to the portion of the needle holder located proximal of the groove 126. As in the embodiment described above, the groove 126 is configured to receive the collar 150 in a manner that allows the collar 150, and the attached sheath 180, to rotate relative to the needle holder 120.

The construction of the collar 150 and the way in which the sheath 180 is pivotally connected to the collar 150 is similar to that described above. The protector 170 is adapted to be placed over the cannula 140 to cover the cannula before the safety needle assembly is used.

The various components forming the safety needle assembly shown in FIGS. 11-16 can be assembled and used in a manner similar to that described above in connection with the embodiment shown in FIGS. 1-10.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A safety needle assembly comprising:
   a syringe barrel having an interior configured to receive a plunger and possessing a proximal end portion and a distal end portion;
   a cannula mounted at the distal end portion of the syringe barrel, the cannula possessing a distal end and a proximal end, the cannula being provided with a lumen;
   a collar formed separately from the syringe barrel and mounted on the syringe barrel, the collar being provided with a pair of spaced apart mounting ears each provided with a hole;
   a protector positioned over the cannula and covering the distal end of the cannula, the protector having an open end and an oppositely located closed end, the protector being removable to expose the cannula including the distal end;
   a sheath provided with an opening extending along at least a portion of a longitudinal extent of the sheath providing access to an interior of the sheath, the sheath comprising a pin mount and a pair of pins extending from the pin mount, each of the pins being positioned in a respective one of the holes in the mounting ears of the collar so that the sheath is pivotally mounted on the collar, the sheath being positioned outside the protector when the protector is positioned over the cannula and being pivotable towards the cannula after removal of the protector so that the cannula is positioned in the interior of the sheath and is covered by the sheath; and
   the pin mounting portion comprising a plurality of flat surfaces which engage a portion of the collar located between the mounting ears during pivoting movement of the sheath.

2. The safety needle assembly according to claim 1, wherein the distal end portion of the syringe barrel is provided with an annular groove in which is positioned the collar.

3. The safety needle assembly according to claim 1, including a plurality of outwardly extending protuberances circumferentially spaced apart on an outer surface of the collar, an inner surface of the protector adjacent the open end of the protector engaging the outwardly extending protuberances when the protector is positioned over the cannula in covering relation to the cannula.

4. The safety needle assembly according to claim 1, wherein the collar is rotatably mounted on the syringe barrel.

5. A safety needle assembly comprising:
   a syringe barrel having an interior configured to receive a plunger;
   a cannula mounted at the syringe barrel, the cannula possessing a distal end and a proximal end, the cannula being provided with a lumen;
   a protector positioned over the cannula and covering the distal end of the cannula, the protector having an open end to permit the protector to be placed in covering relation to the cannula, the protector being removable to expose the cannula;
   a sheath possessing an opening extending along at least a portion of a longitudinal extent of the sheath which provides access to an interior of the sheath, the sheath being pivotally mounted with respect to the syringe barrel to permit the sheath, upon application of a force, to be pivoted in a direction toward the cannula from a non-covering position in which the cannula is exposed after removal of the protector to a covering position in which the cannula is covered by the sheath, the sheath possessing at least one locking tab adapted to engage the cannula when the sheath is sufficiently pivoted toward the cannula to permanently lock the sheath in a locked position relative to the cannula to prevent the sheath from pivoting back towards the non-covering position; and
   the sheath comprising means for causing the sheath to automatically pivot in a direction away from the cannula when said force is removed prior to the cannula being engaged by the locking tab to thereby indicate that the locking tab has not engaged the cannula and the sheath is not in the locked position.

6. The safety needle assembly according to claim 5, further comprising a collar mounted on the syringe barrel, the collar being provided with a sheath mounting portion, and the sheath being pivotally mounted on the sheath mounting portion of the collar.

7. The safety needle assembly according to claim 6, wherein the collar is rotatably mounted on the syringe barrel so that the collar is rotatable about the syringe barrel.

8. The safety needle assembly according to claim 6, wherein the means for causing the sheath to automatically pivot in a direction away from the cannula when said force is removed prior to the cannula being engaged by the locking tab includes a plurality of flat surfaces on the sheath which contact a portion of the collar as the sheath is pivoted toward the locked position.

9. The safety needle assembly according to claim 6, wherein the distal end portion of the syringe barrel is provided with an annular groove in which is positioned the collar.

10. The safety needle assembly according to claim 6, including a plurality of outwardly extending protuberances circumferentially spaced apart on an outer surface of the collar, an inner surface of the protector adjacent the open end of the protector engaging the outwardly extending protuberances when the protector is positioned over the cannula in covering relation to the cannula.

11. The safety needle assembly according to claim 6, wherein the collar includes an outwardly extending annular ridge which is contacted by the open end of the protector when the protector is positioned over the cannula.

12. The safety needle assembly according to claim 5, wherein the means for causing the sheath to automatically pivot in a direction away from the cannula when said force is removed prior to the cannula being engaged by the locking tab includes a plurality of flat surfaces on the sheath.

13. A safety needle assembly comprising:
   a syringe barrel assembly the includes a syringe barrel having an interior configured to receive a plunger;
   a cannula mounted at the syringe barrel, the cannula possessing a distal end and a proximal end, and being provided with a lumen
   a protector positioned over the cannula and covering the distal end of the cannula, the protector having an open end to permit the protector to be placed in covering relation to the cannula, the protector being removable to expose the cannula;
   a sheath possessing an opening extending along at least a portion of a longitudinal extent of the sheath which provides access to an interior of the sheath, the sheath being pivotally mounted on the syringe barrel assembly to permit the sheath to be pivoted relative to the syringe barrel assembly in a direction toward the cannula from a non-covering position in which the cannula is exposed after removal of the protector to a covering position in which the cannula is covered by the sheath, and the sheath comprising a plurality of flat surfaces adapted to successively engage a portion of the syringe barrel assembly as the sheath is pivoted relative to the syringe barrel assembly.

14. The safety needle assembly according to claim 13, further comprising at least one locking tab provided on the interior of the sheath to engage the cannula when the sheath is sufficiently pivoted toward the cannula to permanently lock the sheath in a locked position relative to the cannula to prevent the sheath from pivoting back towards the non-covering position.

15. The safety needle assembly according to claim 13, wherein the collar is rotatably mounted on the syringe barrel so that the collar is rotatable about the syringe barrel.

16. The safety needle assembly according to claim 13, wherein the flat surfaces on the sheath successively engage a portion of an outer surface of the collar as the sheath is pivoted from the non-covering position to the covering position.

17. A safety needle assembly comprising:
- an evacuated tube-receiving tubular needle holder having a hollow interior adapted to receive an evacuated tube, the evacuated tube-receiving tubular needle holder possessing a proximal end portion and a distal end portion;
- a cannula mounted at the distal end portion of the evacuated tube-receiving tubular needle holder, the cannula possessing a distal end and a proximal end, the cannula being provided with a lumen;
- a collar formed separately from the evacuated tube-receiving tubular needle holder and mounted on the evacuated tube-receiving tubular needle holder, the collar being provided with a pair of spaced apart mounting ears each provided with a hole;
- a protector positioned over the cannula and covering the distal end of the cannula, the protector having an open end and an oppositely located closed end, the protector being removable to expose the cannula including the distal end;
- a sheath provided with an opening extending along at least a portion of a longitudinal extent of the sheath providing access to an interior of the sheath, the sheath comprising a pin mount and a pair of pins extending from the pin mount, each of the pins being positioned in a respective one of the holes in the mounting ears of the collar so that the sheath is pivotally mounted on the collar, the sheath being positioned outside the protector when the protector is positioned over the cannula and being pivotable towards the cannula after removal of the protector so that the cannula is positioned in the interior of the sheath and is covered by the sheath; and
- the pin mounting portion comprising a plurality of flat surfaces which engage a portion of the collar located between the mounting ears during pivoting movement of the sheath.

* * * * *